United States Patent
Gauglitz et al.

(10) Patent No.: US 10,921,396 B2
(45) Date of Patent: *Feb. 16, 2021

(54) SYSTEMS AND METHODS FOR SENSING EXTERNAL MAGNETIC FIELDS IN IMPLANTABLE MEDICAL DEVICES

(71) Applicant: Cardiac Pacemakers, Inc., St. Paul, MN (US)

(72) Inventors: Karl Gauglitz, Snohomish, WA (US); Thomas M. Bocek, Seattle, WA (US); Mark Rutzer, Seattle, WA (US); Lorin W. Matthews, Brier, WA (US); William E. Reagor, Bellevue, WA (US); Blair Erbstoeszer, Kirkland, WA (US)

(73) Assignee: Cardiac Pacemakers, Inc., St. Paul, MN (US)

(*) Notice: Subject to any disclaimer, the term of this patent is extended or adjusted under 35 U.S.C. 154(b) by 544 days.

This patent is subject to a terminal disclaimer.

(21) Appl. No.: 15/662,091

(22) Filed: Jul. 27, 2017

(65) Prior Publication Data
US 2017/0322266 A1 Nov. 9, 2017

Related U.S. Application Data

(63) Continuation of application No. 14/204,559, filed on Mar. 11, 2014, now Pat. No. 9,766,307, which is a
(Continued)

(51) Int. Cl.
*G01R 33/28* (2006.01)
*A61N 1/37* (2006.01)
(Continued)

(52) U.S. Cl.
CPC ............ *G01R 33/287* (2013.01); *A61B 5/055* (2013.01); *A61N 1/3605* (2013.01);
(Continued)

(58) Field of Classification Search
CPC ...... A61N 1/3718; A61N 1/08; A61N 1/3605; A61N 1/3956; A61B 5/055
See application file for complete search history.

(56) References Cited

U.S. PATENT DOCUMENTS

| 2,841,763 A | 7/1958 | Williams et al. |
| 2,980,846 A | 4/1961 | Ringelman |

(Continued)

FOREIGN PATENT DOCUMENTS

| GB | 2395276 A | 5/2004 |
| WO | WO-2003037429 A1 | 5/2003 |

OTHER PUBLICATIONS

"U.S. Appl. No. 11/460,081, Advisory Action", 3 pgs.
(Continued)

*Primary Examiner* — Sean P Dougherty
(74) *Attorney, Agent, or Firm* — Schwegman Lundberg & Woessner, P.A.

(57) ABSTRACT

Systems and methods for sensing external magnetic fields in implantable medical devices are provided. One aspect of this disclosure relates to an apparatus for sensing magnetic fields. An apparatus embodiment includes a sensing circuit with at least one inductor having a magnetic core that saturates in the presence of a magnetic field having a prescribed flux density. The apparatus embodiment also includes an impedance measuring circuit connected to the sensing circuit. The impedance measuring circuit is adapted to measure impedance of the sensing circuit and to provide a signal when the impedance changes by a prescribed amount. According to an embodiment, the sensing circuit includes a resistor-inductor-capacitor (RLC) circuit. The impedance measuring circuit includes a transthoracic
(Continued)

impedance measurement module (TIMM), according to an embodiment. Other aspects and embodiments are provided herein.

20 Claims, 4 Drawing Sheets

Related U.S. Application Data continuation of application No. 13/282,968, filed on Oct. 27, 2011, now Pat. No. 8,710,826, which is a continuation of application No. 11/460,081, filed on Jul. 26, 2006, now Pat. No. 8,049,489.

(51) Int. Cl.
| | | |
|---|---|---|
| *G01V 3/10* | (2006.01) | |
| *A61B 5/055* | (2006.01) | |
| *A61N 1/36* | (2006.01) | |
| *A61N 1/39* | (2006.01) | |
| *A61N 1/08* | (2006.01) | |

(52) U.S. Cl.
CPC ......... *A61N 1/3718* (2013.01); *A61N 1/3956* (2013.01); *G01V 3/101* (2013.01); *A61N 1/08* (2013.01)

(56) References Cited

U.S. PATENT DOCUMENTS

| | | | |
|---|---|---|---|
| 3,968,802 | A | 7/1976 | Ballis |
| 4,357,943 | A | 11/1982 | Thompson |
| 4,541,431 | A | 9/1985 | Ibrahim et al. |
| 4,553,095 | A | 11/1985 | Schenk et al. |
| 4,745,923 | A | 5/1988 | Winstrom |
| 5,030,196 | A | 7/1991 | Inoue |
| 5,217,010 | A | 6/1993 | Tsitilk et al. |
| 5,351,004 | A | 9/1994 | Daniels et al. |
| 5,481,238 | A | 1/1996 | Carsten et al. |
| 5,612,862 | A | 3/1997 | Marusik et al. |
| 5,697,958 | A | 12/1997 | Paul et al. |
| 5,759,197 | A | 6/1998 | Sawchuk et al. |
| 6,100,680 | A | 8/2000 | Vig et al. |
| 6,101,417 | A | 8/2000 | Vogel et al. |
| 6,209,764 | B1 | 4/2001 | Hartlaub et al. |
| 6,414,835 | B1 | 7/2002 | Wolf et al. |
| 6,424,145 | B1 | 7/2002 | Woolsey |
| 6,507,189 | B2 | 1/2003 | Woolsey et al. |
| 6,522,920 | B2 | 2/2003 | Silvian et al. |
| 6,564,084 | B2 | 5/2003 | Allred, III et al. |
| 6,741,885 | B1 | 5/2004 | Park et al. |
| 6,795,730 | B2 | 9/2004 | Connelly et al. |
| 6,930,242 | B1 | 8/2005 | Helfer et al. |
| 6,963,779 | B1 | 11/2005 | Shankar |
| 6,971,391 | B1 | 12/2005 | Wang et al. |
| 7,068,030 | B2 | 6/2006 | Hintz et al. |
| 7,076,283 | B2 | 7/2006 | Cho et al. |
| 7,091,412 | B2 | 8/2006 | Wang et al. |
| 7,127,294 | B1 | 10/2006 | Wang et al. |
| 7,151,963 | B2 | 12/2006 | Havel et al. |
| 7,164,950 | B2 | 1/2007 | Kroll et al. |
| 7,295,107 | B2 | 11/2007 | Massengill et al. |
| 7,729,770 | B2 | 6/2010 | Calbelka et al. |
| 7,765,005 | B2 | 7/2010 | Stevenson et al. |
| 7,792,572 | B1 | 9/2010 | Gill et al. |
| 8,049,489 | B2 | 11/2011 | Gauglitz et al. |
| 8,710,826 | B2 | 4/2014 | Gauglitz et al. |
| 2001/0019262 | A1 | 9/2001 | Woolsey et al. |
| 2002/0123682 | A1 | 9/2002 | Allred, III et al. |
| 2003/0078493 | A1 | 4/2003 | Ogawa et al. |
| 2003/0140931 | A1 | 7/2003 | Zeijlemaker et al. |
| 2003/0144704 | A1 | 7/2003 | Terry et al. |
| 2003/0144705 | A1 | 7/2003 | Funke |
| 2004/0017191 | A1 | 1/2004 | Stanley |
| 2004/0046536 | A1 | 3/2004 | Librizzi |
| 2004/0135687 | A1 | 7/2004 | Keene |
| 2004/0139975 | A1 | 7/2004 | Nelson et al. |
| 2004/0210289 | A1 | 10/2004 | Wang et al. |
| 2004/0230271 | A1 | 11/2004 | Wang et al. |
| 2004/0263173 | A1 | 12/2004 | Gray |
| 2004/0267233 | A1 | 12/2004 | Ginggen |
| 2005/0004417 | A1 | 1/2005 | Nelson et al. |
| 2005/0070787 | A1 | 3/2005 | Zeijlemaker |
| 2005/0079132 | A1 | 4/2005 | Wang et al. |
| 2005/0197677 | A1 | 9/2005 | Stevenson |
| 2005/0242804 | A1 | 11/2005 | Hintz et al. |
| 2006/0145691 | A1 | 7/2006 | Massengill et al. |
| 2006/0158331 | A1 | 7/2006 | Massengill et al. |
| 2006/0173295 | A1 | 8/2006 | Zeijlemaker |
| 2006/0264730 | A1 | 11/2006 | Stivoric et al. |
| 2007/0080767 | A1 | 4/2007 | Kuzmenka |
| 2007/0083244 | A1 | 4/2007 | Stevenson et al. |
| 2007/0150022 | A1 | 6/2007 | Ujhazy et al. |
| 2007/0191914 | A1 | 8/2007 | Stessman |
| 2008/0071168 | A1 | 3/2008 | Gauglitz et al. |
| 2012/0046707 | A1 | 2/2012 | Gauglitz et al. |
| 2014/0194729 | A1 | 7/2014 | Gauglitz et al. |

OTHER PUBLICATIONS

"U.S. Appl. No. 11/460,081, Advisory Action dated May 19, 2010", 3 pgs.

"U.S. Appl. No. 11/460,081, Final Office Action dated Jun. 22, 2010", 13 pgs.

"U.S. Appl. No. 11/460,081, Final Office Action dated Feb. 8, 2010", 13 pgs.

"U.S. Appl. No. 11/460,081, Non Final Office Action dated Jan. 21, 2011", 9 pgs.

"U.S. Appl. No. 11/460,081, Non-Final Office Action dated Jan. 12, 2009", 9 pgs.

"U.S. Appl. No. 11/460,081, Non-Final Office Action dated Aug. 20, 2009", 12 Pgs.

"U.S. Appl. No. 11/460,081, Notice of Allowance dated Jul. 19, 2011", 11 pgs.

"U.S. Appl. No. 11/460,081, Response filed Apr. 27, 2009 to Non Final Office Action dated Jan. 12, 2009", 9 pgs.

"U.S. Appl. No. 11/460,081, Response filed Sep. 21, 2010 to Final Office Action dated Jun. 22, 2010", 9 pgs.

"U.S. Appl. No. 11/460,081, Response filed Oct. 17, 2008 to Restriction Requirement dated Sep. 26, 2008", 5 pgs.

"U.S. Appl. No. 11/460,081, Response filed Nov. 20, 2009 to Non Final Office Action dated Aug. 20, 2009", 9 pgs.

"U.S. Appl. No. 11/460,081, Response filed Apr. 18, 2011 to Non Final Office Action dated Jan. 21, 2011", 12 pgs.

"U.S. Appl. No. 11/460,081, Response filed May 10, 2010 to Final Office Action dated Feb. 8, 2010", 8 pgs.

"U.S. Appl. No. 11/460,081, Restriction Requirement dated Sep. 26, 2008", 6 pgs.

"U.S. Appl. No. 13/282,968 , Response filed Jul. 1, 2013 to Final Office Action dated May 2, 2013", 7 pgs.

"U.S. Appl. No. 13/282,968, Final Office Action dated May 2, 2013", 7 pgs.

"U.S. Appl. No. 13/282,968, Non Final Office Action dated Jul. 18, 2013", 6 pgs.

"U.S. Appl. No. 13/282,968, Non Final Office Action dated Nov. 20, 2012", 9 pgs.

"U.S. Appl. No. 13/282,968, Notice of Allowance dated Dec. 9, 2013", 10 pgs.

"U.S. Appl. No. 13/282,968, Response filed Feb. 20, 2013 to Non Final Office Action dated Nov. 20, 2012", 7 pgs.

"U.S. Appl. No. 13/282,968, Response filed Oct. 8, 2013 to Non Final Office Action dated Jul. 18, 2013", 5 pgs.

"U.S. Appl. No. 13/282,968, Response filed Sep. 26, 2012 to Restriction Requirement dated Sep. 5, 2012", Response to Restriction Requirement, 7 pgs.

"U.S. Appl. No. 13/282,968, Restriction Requirement dated Sep. 5, 2012", 6 pgs.

(56) References Cited

OTHER PUBLICATIONS

"U.S. Appl. No. 14/204,559, Final Office Action dated Feb. 16, 2017", 6 pgs.
"U.S. Appl. No. 14/204,559, Non Final Office Action dated Aug. 19, 2016", 18 pgs.
"U.S. Appl. No. 14/204,559, Notice of Allowance dated May 15, 2017", 9 pgs.
"U.S. Appl. No. 14/204,559, Preliminary Amendment filed Mar. 12, 2014", 5 pgs.
"U.S. Appl. No. 14/204,559, Response filed Apr. 17, 2017 to Final Office Action dated Feb. 16, 2017", 6 pgs.
"U.S. Appl. No. 14/204,559, Response filed May 23, 2016 to Restriction Requirement dated Mar. 22, 2016", 6 pgs.
"U.S. Appl. No. 14/204,559, Response filed Nov. 21, 2016 to Non Final Office Action dated Aug. 19, 2016", 10 pgs.
"U.S. Appl. No. 14/204,559, Restriction Requirement dated Mar. 22, 2016", 8 pgs.

SYSTEMS AND METHODS FOR SENSING EXTERNAL MAGNETIC FIELDS IN IMPLANTABLE MEDICAL DEVICES

CLAIM OF PRIORITY

This application is a continuation of and claims the benefit of priority under 35 U.S.C. § 120 to U.S. patent application Ser. No. 14/204,559, filed on Mar. 11, 2014, which is a continuation of and claims the benefit of priority under 35 U.S.C. § 120 to U.S. patent application Ser. No. 13/282,968, filed on Oct. 27, 2011, now issued as U.S. Pat. No. 8,710, 826, which is a continuation of and claims the benefit of priority under 35 U.S.C. § 120 to U.S. patent application Ser. No. 11/460,081, filed on Jul. 26, 2006, now issued as U.S. Pat. No. 8,049,489, which is hereby incorporated by reference herein in its entirety.

TECHNICAL FIELD

This disclosure relates to implantable medical devices, particularly systems and methods for sensing external magnetic fields in implantable medical devices.

BACKGROUND

Implantable medical devices (IMDs) include devices such as implantable defibrillators, cardioverters, neurostimulators, and pacemakers. Since the early 1980s, thousands of patients prone to irregular and sometimes life threatening heart rhythms have had IMDs implanted in their bodies, typically in the upper chest area above their hearts. Certain of these devices detect onset of abnormal heart rhythms and automatically apply corrective electrical therapy, specifically one or more bursts of electric energy, to hearts. When the bursts of electric current are of sufficient amplitude and are properly synchronized with the cardiac signal, they restore normal heart function without human intervention, sparing patients considerable discomfort and often saving their lives.

With the increase in use of magnetic resonance imaging (MRI) as a diagnostic tool, patients with IMDs are exposed to strong magnetic fields on a more frequent basis.

SUMMARY

Disclosed herein, among other things, is an apparatus for sensing magnetic fields. An apparatus embodiment includes a sensing circuit with at least one inductor having a magnetic core that saturates in the presence of a magnetic field having a prescribed flux density. The apparatus embodiment also includes an impedance measuring circuit connected to the sensing circuit. The impedance measuring circuit is adapted to measure impedance of the sensing circuit and to provide a signal when the impedance changes by a prescribed amount.

An apparatus embodiment includes means for sensing the presence of a magnetic field from a magnetic resonance imaging device. This apparatus embodiment also includes means for measuring impedance connected to the sensing means, including means for signaling when the measured impedance changes by a prescribed amount. The means for sensing includes a resistor-inductor-capacitor (RLC) circuit, according to various embodiments. According to an embodiment, the means for measuring includes a transthoracic impedance measurement module (TIMM).

One aspect of this disclosure relates to an implantable medical device with magnetic field sensing capability. The device embodiment includes a sensing circuit with at least one inductor having a magnetic core that saturates in the presence of a magnetic field having a prescribed flux density. The device embodiment also includes an impedance measuring circuit connected to the sensing circuit. The impedance measuring circuit is adapted to measure the impedance of the sensing circuit and to provide a signal when the impedance changes by a prescribed amount. The device embodiment further includes a controller adapted to receive the signal and modify device behavior while in the presence of the magnetic field.

One aspect of this disclosure relates to a method for sensing external magnetic fields. The method embodiment includes sensing a magnetic field using a circuit having an inductor with a magnetic core that saturates in the presence of a magnetic field having a prescribed flux density, measuring impedance of the circuit, and sending a signal to an implantable medical device when the measured impedance indicates the inductor is saturated.

This Summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

DETAILED DESCRIPTION

The following detailed description refers to the accompanying drawings which show, by way of illustration, specific aspects and embodiments in which the present invention may be practiced. These embodiments are described in sufficient detail to enable those skilled in the art to practice the invention. Other embodiments may be utilized and structural, logical, and electrical changes may be made without departing from the scope of the present invention.

System for Sensing External Magnetic Fields

Figure 1:
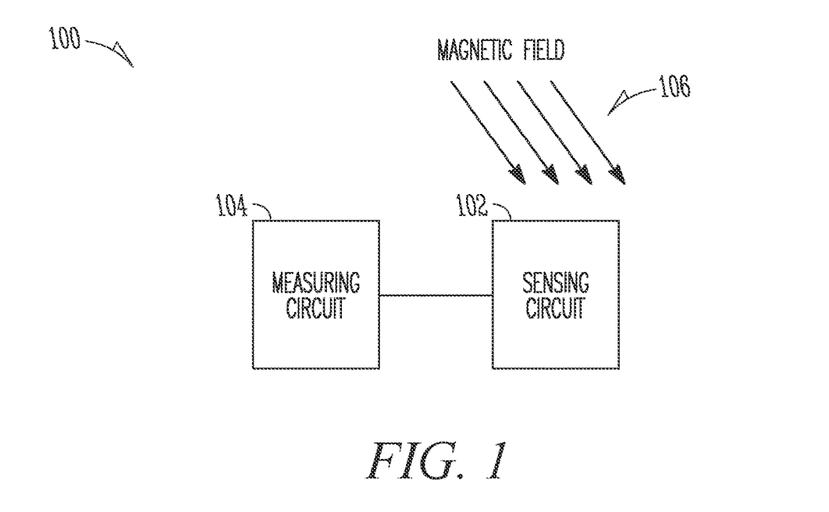
FIG. 1 illustrates a block diagram of a system for sensing magnetic fields, according to one embodiment.

FIG. 1 illustrates a block diagram of a system for sensing magnetic fields, according to one embodiment. The depicted apparatus 100 includes a sensing circuit 102 connected to an impedance measuring circuit 104. The sensing circuit 102 has at least one inductor having a magnetic core that saturates in the presence of a magnetic field 106 having a prescribed flux density. The impedance measuring circuit 104 is adapted to measure impedance of the sensing circuit and to provide a signal when the impedance changes by a prescribed amount. According to various embodiments, the impedance measuring circuit includes a transthoracic impedance measurement module (TIMM). The impedance measuring circuit delivers a current pulse to the sensing circuit to measure impedance, according to various embodiments. According to one embodiment, the impedance measuring circuit delivers a current pulse to the sensing circuit periodically.

According to various embodiments, the sensing circuit includes a resistor-inductor-capacitor (RLC) circuit. The impedance of the inductor changes upon saturation of the magnetic core, which changes the impedance of the RLC circuit containing the inductor. The impedance measuring circuit provides the signal to an implantable medical device, and the device modifies a behavior after receiving the signal, in various embodiments. Modifying device behavior may include changing to a pacing mode, changing to a tachy mode, changing lead configuration, or changing to a protect mode, according to various embodiments. Other types of device behavior or characteristics may be changed or modified upon receipt of the signal without departing from the scope of this disclosure.

According to an embodiment, the inductor or inductors include a ferrite drum core inductor. Other types of inductors can be used. Examples include, but are not limited to: gapped toroidal inductors or tape wound core inductors. According to various embodiments, the inductor or inductors include an isotropic material, so that the inductor(s) saturate as a result of magnetic field intensity only, independent of direction. According to various embodiments, the inductor is sized to fit within the housing of an implantable medical device. The inductor has maximum dimensions of 0.4 inches in width, 0.4 inches in length and 0.3 inches in height, according to one embodiment.

An apparatus embodiment includes means for sensing the presence of a magnetic field from a magnetic resonance imaging device. This apparatus embodiment also includes means for measuring impedance connected to the sensing means, including means for signaling when the measured impedance changes by a prescribed amount. The means for sensing includes a resistor-inductor-capacitor (RLC) circuit, according to various embodiments. According to an embodiment, the means for measuring includes a transthoracic impedance measurement module (TIMM). According to various embodiments, the means for sensing includes an inductor having a magnetic core that saturates at a selected magnetic flux density. The selected magnetic flux density includes a flux density of a Magnetic Resonance Imaging (MRI) machine, in an embodiment. The prescribed amount of impedance change includes a difference in impedance caused by saturation of the magnetic core, in various embodiments. The means for sensing includes an RLC circuit in an embodiment. Other types of sensing circuits having inductive elements capable of impedance changes at a prescribed flux density can be used. The means for measuring includes a TIMM in various embodiments. Other types of circuits able to measure impedance or detect a parameter indicative of impedance can be used without departing from the scope of this disclosure. According to various embodiments, detecting a parameter indicative of impedance includes detecting phase shift. The saturable magnetics described need not be a single inductor, but may include multiple inductors in a variety of orientations. The means for measuring can include a controller in various embodiments.

Figure 2:
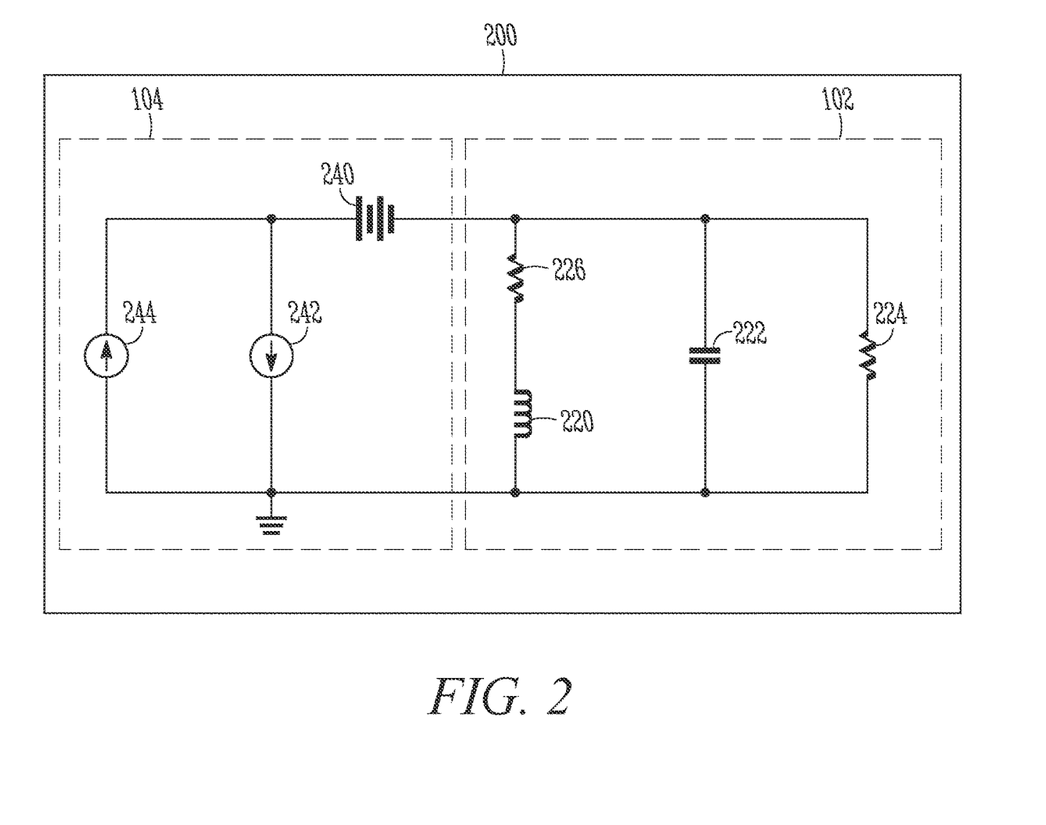
FIG. 2 illustrates a schematic diagram of a system for sensing magnetic fields, according to one embodiment.

FIG. 2 illustrates a schematic diagram of a system for sensing magnetic fields, according to one embodiment. The depicted apparatus 200 includes a sensing circuit 102 connected to an impedance measuring circuit 104. The sensing circuit 102 has at least one inductor 220 having a magnetic core that saturates in the presence of a magnetic field having a prescribed flux density. The impedance measuring circuit 104 is adapted to measure impedance of the sensing circuit and to provide a signal when the impedance changes by a prescribed amount.

According to various embodiments, the impedance measuring circuit 104 includes a transthoracic impedance measurement module (TIMM). The TIMM includes at least one voltage source 240 and a first current source 244 and second current source 242. The two current sources depicted in the figure are not essential, and a single source can by used so long as the source can provide both positive and negative current pulses to the sensor circuit. According to various embodiments, the sensing circuit includes a resistor-inductor-capacitor (RLC) circuit. In the depicted embodiment, the resistor 224, the capacitor 222 and the inductor 220 are connected in parallel. Other types of circuits, including series RLC circuits, can be used without departing from the scope of this disclosure. A second resistor 226 is shown in series with the inductor 220.

Saturable Magnetics

As discussed in FIG. 1 above, a system is provided for sensing magnetic fields using saturable magnetics. Saturable magnetics refers to the properties of a magnetic core around which the inductive coil is wound. The magnetic core will saturate when in the presence of a magnetic field with a strength (or flux density) at the level which causes all of the magnetic moments in the core material to line up with the applied magnetizing force. If an inductor has a saturated core, no further magnetic flux will result from further increases in current, and so there will be no voltage induced in opposition to the change in current. Thus, an inductor loses its inductance, or ability to oppose changes in current, when its core becomes magnetically saturated. If an inductor's inductance changes, then its reactance (and impedance) to AC current changes as well.

Figure 3:
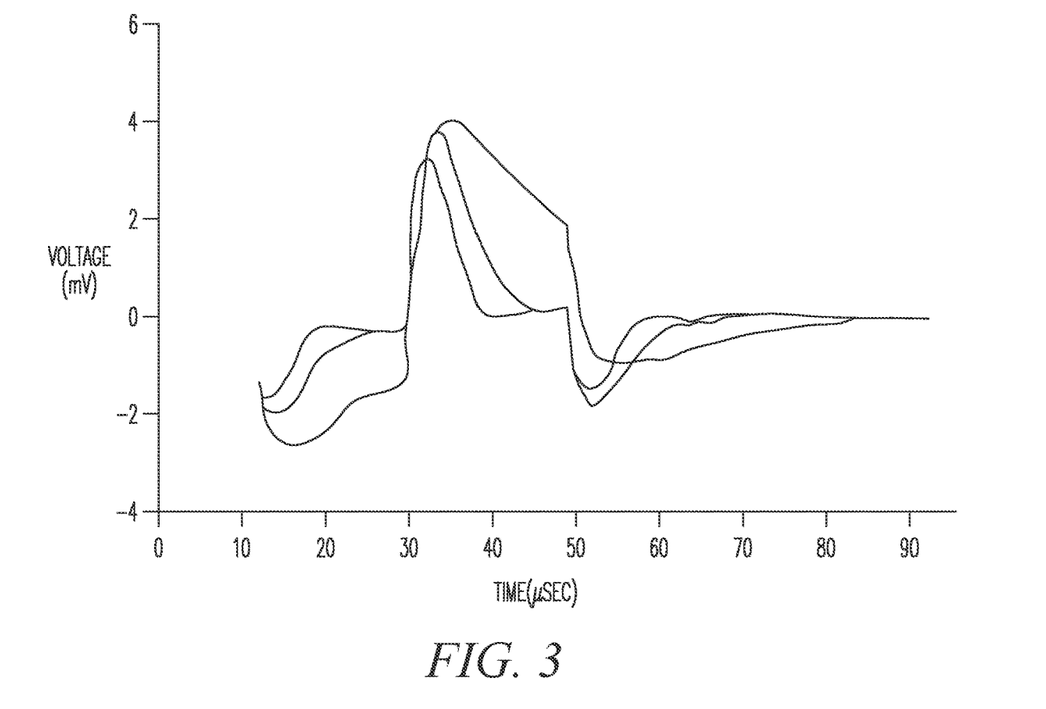
FIG. 3 illustrates a graphical diagram of measured impedance in a system for sensing magnetic fields, according to one embodiment.

As stated above, the inductor is selected with a magnetic core that saturates at a prescribed flux density. The flux density is chosen to cause saturation in the presence of a chosen magnetic field (such as that of an MRI device). Once this flux density is reached, the inductance, and therefore the impedance, of the sensor circuit drops dramatically. The measurement circuit measures the impedance of the sensing circuit at programmed intervals. According to various embodiments, impedance of the sensing circuit is measured at a frequency from 1 kHz to 1 MHz. According to one embodiment, a current pulse is generated at 20 Hz. The impedance of the sensing circuit is measured once every 30 seconds, in an embodiment. FIG. 3 illustrates a graphical diagram of measured impedance in a system for sensing magnetic fields, according to one embodiment. As shown in the drawing, the point at which the inductor's magnetic core saturates is when the voltage (for a given current) across the sensing circuit decreases significantly.

Implantable Medical Devices

Figure 4:
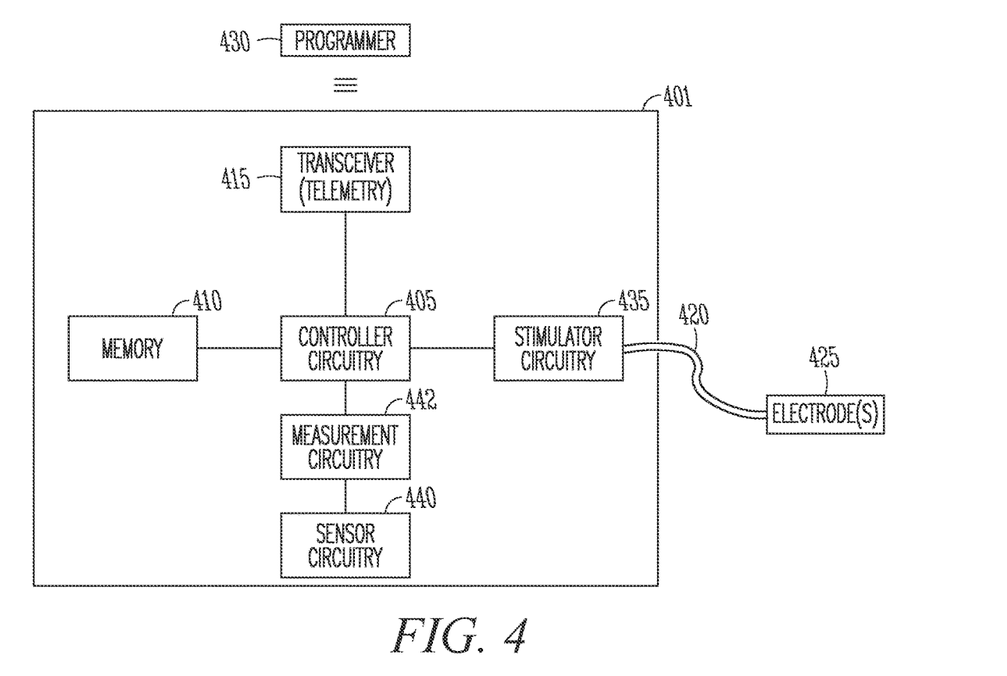
FIG. 4 illustrates a block diagram of a system with an IMD including a system for sensing magnetic fields, according to one embodiment.

FIG. 4 illustrates a block diagram of a system with an IMD including a system for sensing magnetic fields, according to one embodiment. The system includes an implantable medical device (IMD) 401, an electrical lead 420 coupled to the IMD 401, and at least one electrode 425. The IMD includes a controller circuit 405, a memory circuit 410, a telemetry circuit 415, and a stimulation circuit 435. The controller circuit 405 is operable on instructions stored in the memory circuit to deliver an electrical stimulation therapy. Therapy is delivered by the stimulation circuit 435 through the lead 420 and the electrode(s) 425. The telemetry circuit 415 allows communication with an external programmer 430. The programmer 430 can be used to adjust the programmed therapy provided by the IMD 401, and the IMD can report device data (such as battery and lead resistance) and therapy data (such as sense and stimulation data) to the programmer using radio telemetry, for example. The illustrated system also includes sensor circuitry 440 with at least one inductor having a magnetic core that saturates in the presence of a magnetic field having a prescribed flux density. The device embodiment also includes an impedance measuring circuit 442 connected to the sensing circuit, the impedance measuring circuit adapted to measure the impedance of the sensing circuit and to provide a signal when the impedance changes by a prescribed amount. The controller circuit 405 is adapted to receive the signal and modify device behavior while in the presence of the magnetic field, according to various embodiments. According to various embodiments, the IMD 401 senses a magnetic field using the sensing circuit, measures the impedance of the sensing circuit using the measurement circuit, and sends a signal using the controller when the measured impedance indicates the inductor is saturated, as disclosed in the method depicted in FIG. 6, described below. While the sensor and measurement circuitry are shown within the device, either or both of them may be located outside the IMD without departing from the scope of the disclosure.

According to various embodiments, the impedance measuring circuit includes a transthoracic impedance measurement module (TIMM). The sensing circuit includes a resistor-inductor-capacitor (RLC) circuit, according to various embodiments. In an embodiment, the sensing circuit includes multiple inductors oriented in more than one direction. The prescribed flux density includes flux density of a Magnetic Resonance Imaging (MRI) machine, according to one embodiment. According to various embodiments, the disclosed systems and methods can be used with a leadless device. For example, in an embodiment, one or more satellite electrodes are controlled wirelessly to deliver electrical therapy.

Figure 5:
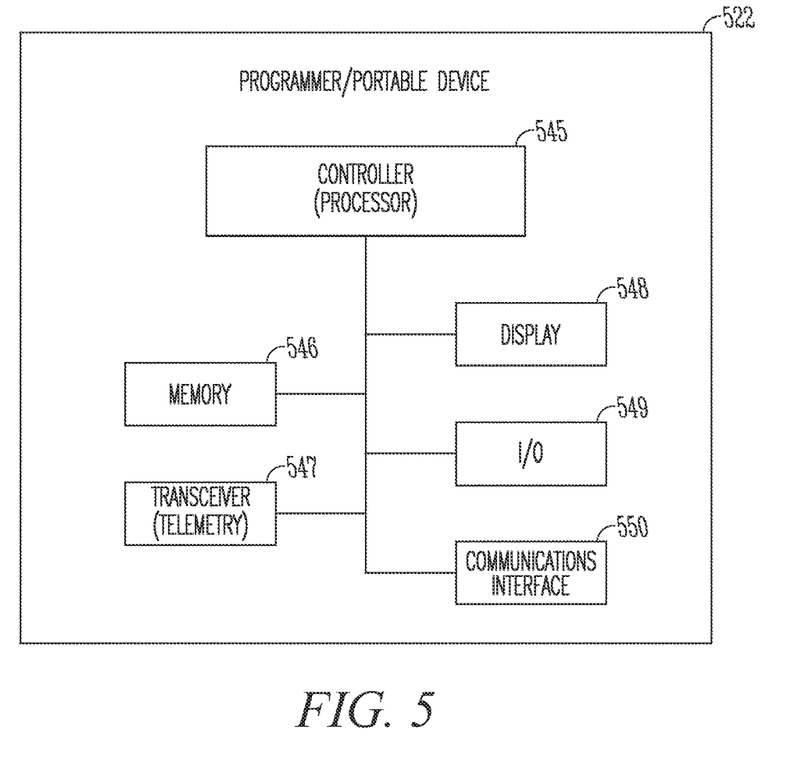
FIG. 5 illustrates a block diagram of a programmer such as illustrated in the system of FIG. 4 or other external device to communicate with the IMD(s), according to one embodiment.

FIG. 5 illustrates a programmer 522, such as the programmer 430 illustrated in the system of FIG. 4 or other external device to communicate with the implantable medical device(s), according to one embodiment. Examples of other external devices include Personal Digital Assistants (PDAs), personal laptop and desktop computers in an Advanced Patient Management (APM) system, or a handheld device such as an Advance Partner system. The illustrated device 522 includes controller circuitry 545 and a memory 546. The controller circuitry 545 is capable of being implemented using hardware, software, and combinations of hardware and software. For example, according to various embodiments, the controller circuitry 545 includes a processor to perform instructions embedded in the memory 546 to perform a number of functions, including communicating data and/or programming instructions to the implantable devices. The illustrated device 522 further includes a transceiver 547 and associated circuitry for use to communicate with an implantable device. Various embodiments have wireless communication capabilities. For example, various embodiments of the transceiver 547 and associated circuitry include a telemetry coil for use to wirelessly communicate with an implantable device. The illustrated device 522 further includes a display 548, input/output (I/O) devices 549 such as a keyboard or mouse/pointer, and a communications interface 550 for use to communicate with other devices, such as over a communication network.

Methods for Sensing External Magnetic Fields

Figure 6:
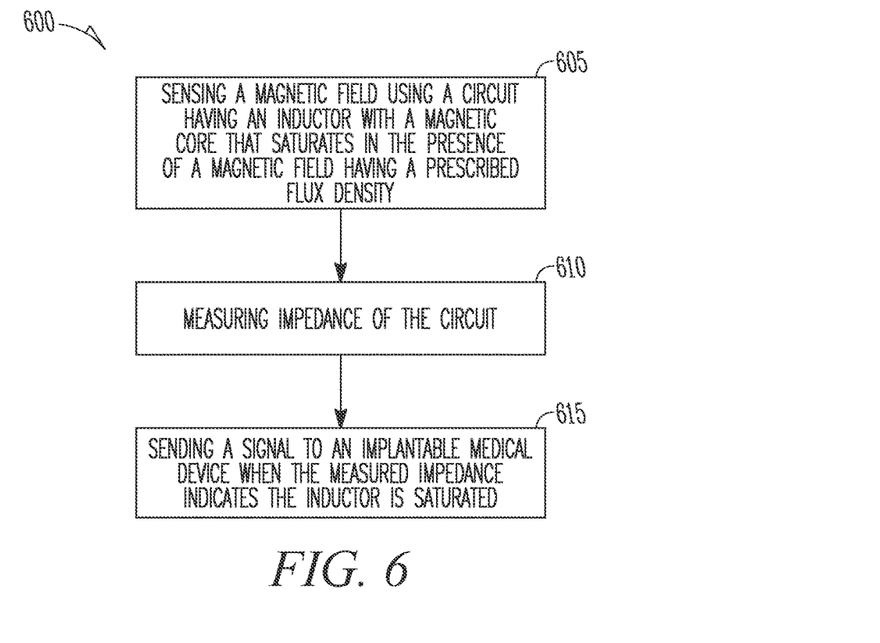
FIG. 6 illustrates a flow diagram of a method for sensing external magnetic fields from an IMD, according to one embodiment.

FIG. 6 illustrates a flow diagram of a method for sensing external magnetic fields from an IMD, according to one embodiment. The method 600 embodiment includes sensing a magnetic field using a circuit having an inductor with a magnetic core that saturates in the presence of a magnetic field having a prescribed flux density, at 605. The method embodiment also includes measuring impedance of the circuit, at 610, and sending a signal to an implantable medical device when the measured impedance indicates the inductor is saturated, at 615. According to various embodiments, the method further includes modifying behavior of the implantable medical device upon receipt of the signal. Modifying device behavior may include changing to a pacing mode, changing to a tachy mode, changing lead configuration, or changing to a protect mode, according to various embodiments. Other types of device behavior or characteristics may be changed or modified upon receipt of the signal without departing from the scope of this disclosure.

According to various embodiments, measuring impedance of the circuit includes measuring impedance of the circuit by providing a current pulse to the circuit and measuring voltage across the circuit. The impedance may also be measured by providing a known voltage across the circuit and measuring the current through the circuit. Other methods for measuring impedance of the circuit may be used without departing from the scope of this disclosure.

Methods for Making a Magnetic Field Sensor

Figure 7:
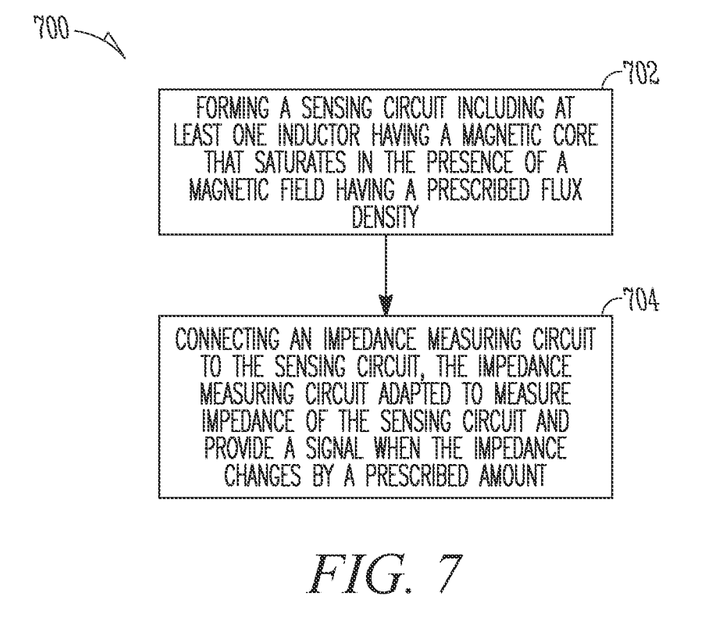
FIG. 7 illustrates a flow diagram of a method for making a magnetic field sensor, according to one embodiment.

FIG. 7 illustrates a flow diagram of a method for making a magnetic field sensor, according to one embodiment. An embodiment of the method 700 includes forming a sensing circuit, at 702. According to various embodiments, forming a sensing circuit includes forming a circuit with at least one inductor having a magnetic core that saturates in the presence of a magnetic field having a prescribed flux density. According to an embodiment, the prescribed flux density is that of an MRI device. The method embodiment also includes connecting an impedance measuring circuit to the sensing circuit, at 704. According to various embodiments, the impedance measuring circuit is adapted to measure impedance of the sensing circuit and provide a signal when the impedance changes by a prescribed amount. In one embodiment, the method also includes connecting a controller to the impedance measuring circuit, the controller adapted to receive the signal and modify behavior of an implantable medical device while in the presence of the magnetic field. The controller may modify device behavior to protect the device from damage due to the presence of the magnetic field, in various embodiments.

The present disclosure provides systems and methods for sensing external magnetic fields in implantable medical devices. The systems function as an omnidirectional MRI detection circuit capable of signaling the IMD to indicate the presence of a strong magnetic field. The described systems and methods have several advantages, including but not limited to: eliminating false charge timeouts that occur in devices when attempting to charge while magnetics are saturated; preventing induced currents from flowing in a lead system; and, as mentioned above, allowing an implantable device to modify its behavior when exposed to strong magnetic fields.

The described systems and methods can be implemented as part of an implantable device, or separate from and in conjunction with the device. Types of devices that can benefit from the described systems and methods include, but are not limited to: cardiac resynchronization therapy (CRT) devices, defibrillators, pacemakers and neural stimulators.

One of ordinary skill in the art will understand that, the modules and other circuitry shown and described herein can be implemented using software, hardware, and combinations of software and hardware. As such, the illustrated modules and circuitry are intended to encompass software implementations, hardware implementations, and software and hardware implementations.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. A method, comprising:
    sensing, using a sensing circuit, the presence of a magnetic field from a magnetic resonance imaging device, including using an isotropic material adapted to saturate as a result of magnetic field intensity independent of direction; and
    measuring impedance connected to the isotropic material at programmed intervals; and
    signaling, using a control circuit, when the measured impedance of the isotropic material changes by a prescribed amount.

2. The method of claim 1, wherein sensing the presence of a magnetic field includes using an inductor.

3. The method of claim 2, wherein the inductor includes a magnetic core.

4. The method of claim 3, wherein the magnetic core saturates at a selected magnetic flux density.

5. The method of claim 4, wherein the selected magnetic flux density includes a flux density of a Magnetic Resonance Imaging (MRI) machine.

6. The method of claim 3, wherein the prescribed amount includes a difference in impedance caused by saturation of the magnetic core.

7. The method of claim 1, wherein sensing the presence of a magnetic field includes using an RLC circuit.

8. The method of claim 1, wherein measuring impedance includes using a TIMM, the TIMM configured to measure impedance of the isotropic material.

9. The method of claim 1, wherein measuring impedance includes using a controller.

10. The method of claim 1, wherein
    the sensing circuit includes multiple inductors, each of the multiple inductors oriented in a different direction and having a magnetic core that saturates in the presence of the magnetic field having a flux density of the magnetic resonance imaging (MRI) device independent of direction, to sense the presence of the magnetic field near an implantable medical device (IMD); and
    wherein the control circuit includes a control module connected to the sensing circuit to monitor the inductors and to send a signal to the IMD when at least one of the inductors saturates.

11. The method of claim 10, comprising using the control module to measure impedance of a circuit including the inductor.

12. The method of claim 11, comprising using the control module to measure impedance of a circuit including the inductor at a frequency from 1 kHz to 1 MHz.

13. The method of claim 11, comprising using the control module to measure impedance of a circuit including the inductor at a frequency of 20 Hz.

14. A system, comprising:
    a sensing circuit configured to sense the presence of a magnetic field from a magnetic resonance imaging device, including using an isotropic material adapted to saturate as a result of magnetic field intensity independent of direction; and
    a measuring circuit configured to measure impedance connected to the isotropic material at programmed intervals; and
    a control circuit configured to provide a signal when the measured impedance of the isotropic material changes by a prescribed amount.

15. The system of claim 14, wherein the sensing circuit includes an inductor.

16. The system of claim 15, wherein the inductor includes a magnetic core.

17. The system of claim 16, wherein the magnetic core saturates at a selected magnetic flux density.

18. The system of claim 17, wherein the selected magnetic flux density includes a flux density of a Magnetic Resonance Imaging (MRI) machine.

19. The system of claim 14, wherein the measuring circuit includes a transthoracic impedance measurement module (TIMM) configured to measure impedance of the isotropic material.

20. The system of claim 14, wherein the measuring circuit includes a controller.

* * * * *